United States Patent
Bordoloi et al.

(10) Patent No.: US 8,912,357 B2
(45) Date of Patent: Dec. 16, 2014

(54) METHOD FOR THE EXTRACTION OF SHIKIMIC ACID

(75) Inventors: Manobjyoti Bordoloi, Assam (IN); Jayanta Borah, Assam (IN); Dipak Kumar Roy, Assam (IN); Subhash Chandra Dutta, Assam (IN); Nabin Chandra Baruah, Assam (IN); Paruchuri Gangadhar Rao, Assam (IN)

(73) Assignee: Council of Scientific & Industrial Research, New Delhi (IN)

( * ) Notice: Subject to any disclaimer, the term of this patent is extended or adjusted under 35 U.S.C. 154(b) by 273 days.

(21) Appl. No.: 13/583,315

(22) PCT Filed: Mar. 9, 2011

(86) PCT No.: PCT/IB2011/000501
§ 371 (c)(1),
(2), (4) Date: Dec. 12, 2012

(87) PCT Pub. No.: WO2011/110927
PCT Pub. Date: Sep. 15, 2011

(65) Prior Publication Data
US 2013/0137895 A1      May 30, 2013

(30) Foreign Application Priority Data

Mar. 12, 2010   (IN) .............................. 575/DEL/2010

(51) Int. Cl.
*C07C 51/47* (2006.01)
*C07C 51/43* (2006.01)
*C07C 51/44* (2006.01)

(52) U.S. Cl.
CPC ................. *C07C 51/44* (2013.01); *C07C 51/47* (2013.01); *C07C 51/43* (2013.01)
USPC ........................................................ 562/508

(58) Field of Classification Search
CPC .......... C07C 51/47; C07C 51/53; C07C 51/44
USPC ........................................................ 562/508
See application file for complete search history.

(56) References Cited

PUBLICATIONS

CN 101070281—Google translation 2006.*

* cited by examiner

*Primary Examiner* — Yevegeny Valenrod
(74) *Attorney, Agent, or Firm* — Buchanan Ingersoll & Rooney PC

(57) ABSTRACT

This invention is directed to the production of shikimic acid from *Illicium griffithii* fruits. The method according to the invention is particularly applicable to the isolation of shikimic acid from *Illicium griffithii* fruits (seeds and pericarps). Yield is 12-18% w/w. Shikimic acid is useful as raw material for the production of oseltavir (Tamiflu) used against Avian Flu. It is also reported that its triacyl derivatives can inhibit blood platelet assembling and Thrombosis by affecting the metabolism of Arachidonic acid. Hitherto known commercial methods of production of shikimic acid from the fruits of star anise (*Illicium verum*) and sweet gum (*Liquidambar styraciflua*) gives only 3-7% and 1.5% respectively. The price of shikimic acid in the international market varies from US$ 45.00 to 1000.00 per Kg depending on demand. Further as per report published at the website www.livemint.com, China Government has imposed restriction on export of shikimic acid.

7 Claims, No Drawings

METHOD FOR THE EXTRACTION OF SHIKIMIC ACID

CROSS-REFERENCE TO RELATED APPLICATIONS

This application is a U.S. National Stage patent application pursuant to 35 U.S.C. §371 of International Patent Application PCT/IB2011/000501, filed on Mar. 9, 2011, and published as WO 2011/110927 on Sep. 15, 2011, which claims priority to India Patent Application 575/DEL/2010, filed on Mar. 12, 2010, all of which are incorporated herein by reference in their entireties for all purposes.

FIELD OF THE INVENTION

The present invention relates to a method for the extraction of highly pure (3R,4S,5R)-(−)-3,4,5-trihydroxy-1-cyclohexenecarboxylic acid (L-Shikimic acid) from the fruits (seeds and pericarps) of *Illicium griffitii*.

Present invention further relates to a method for the production of high purity shikimic acid, useful for the production of avian flu drug Tamiflu (Oseltamivir).

More particularly, this invention relates to the isolation of the natural levorotatory L-shikimic acid from the fruits of *Illicium griffithii* occurring in Arunachal Pradesh of north eastern India through the use of hexane, petroleum ether, chloroform, dichloromethane, ethylene dichloride, ethyl acetate, methyl acetate, propyl acetate, methanol, ethanol, propanol, butanol or combination of two or more solvents followed by crystallization technique utilizing an alcohol such as methanol, ethanol or propanol. Optionally but not essentially, organic acid such as acetic acid can also be used for recrystallization purpose.

BACKGROUND OF THE INVENTION

Shikimic acid is useful as starting materials for antibacterial, antifungal, herbicidal agents and as nutritional. Originally shikimic acid was isolated from Japanese star anise (Botanical name—*Illicium anise* family—Illiciaceae) in trace amount. Later on, it was found to occur in many plants in very trace amount. Then, it was found that shikimic acid is an intermediate metabolite in the common or shikimate pathway of plants and microorganisms. However, only two plant species of the world are found to accumulate this polyhydroxy aromatic acid in more amount, namely in seeds of Star Anise (Botanical name *Illicium verum*, family—Illiciaceae) and Sweet gum tree (Botanical Name—*Liquidambar styraciflu*). Although, there are 42 species of the genus *Illicium* are available in nature, only one species (i.e. *Illicium verum*) is useful for the production of shikimic acid with a yield of maximum 7% w/w.

*I. griffithii* (Hook. f. & Thorns.) belongs to family Illiciaceae, and is one of the most frequently occurring *Illicium* species in the world. In Arunachal Pradesh, it is locally known as 'Lissi'. It is a small to medium sized tree, which occurs in subtropical and temperate broad-leaved forests of West Kameng, Tawang, Lohit and Lower Subansiri districts and is widely distributed in Bomdila, West Kameng district. Fruits of *I. griffithii* are used in the spice industries. (Reference: R. Duchok, K. Kent, A. Devi Khumbongmayum, A. Paul and M. L. Khan; Population structure and regeneration status of medicinal tree *Illicium griffithii* in relation to disturbance gradients in temperate broad-leaved forest of Arunachal Pradesh; Current Science, Vol. 89, No. 4, 25 August 2005, page 673)

References may be made to U.S. Pat. No. 3,546,072, wherein Araki et al. discloses that 5-dehydroshikimic acid can be prepared by culturing a 5-dehydroshikimic acid producing microorganism of the genus *Corynebacterium* in a culture medium (fermentation broth), containing a carbon source, a nitrogen source, inorganic material and nutrients. The produced and accumulated 5-dehydroshikimic acid is isolated from the culture medium, after filtration to remove the microbial cells, through an adjustment of pH and the addition of active carbon. The active carbon absorbs the 5-dehydroshikimic acid and is eluted with 98% ethanol. The eluate is concentrated under reduced pressure and then the product precipitated from ethanol. This reference does not suggest or disclose the use of an organic acid such as acetic acid to enhance the precipitation of highly pure shikimic acid crystals from an aqueous fermentation broth.

References may be made to U.S. Pat. No. 4,769,061, wherein Comai discloses a genetically modified plant wherein a gene encoding for a mutated glyphosate resistant 5-enolpyruvyl-3-phosphoskimimate synthase enzyme is included in the genome of the plant. This reference makes no suggestion of how to isolate shikimic acid from the tissue of such a genetically modified plant.

References may be made to U.S. Pat. No. 5,214,165, wherein Sutherland et al. relates to 6-fluoroshikimic acid derivatives that have antibacterial, antifungal and herbicidal activity. This reference does not suggest the use of genetically modified microorganisms nor the use of glyphosate addition to a fermentation process to increase the production of shikimic acid. This reference further fails to suggest the use of an organic acid to assist in the isolation of shikimic acid from a fermentation broth. This reference does, however, disclose a class of PCCAs that are useful in the process of this invention.

References may be made to U.S. Pat. No. 5,605,818, wherein Katsumata et al. discloses a process for producing an aromatic amino acid, such as tryptophan, through the use of culturing in a medium a mutant strain of the genus *Corynebacterium* or *Brevibacterium*.

These mutant strains are capable of producing the desired aromatic amino acid and also have a higher transketolase activity than that of the parent strain. The desired aromatic amino acid is accumulated in the culture and recovered therefrom. This reference makes no suggestion of the use of an organic acid to isolate the desired PCCA from the broth. This reference does disclose a number of microorganisms that may produce a fermentation broth that is useful in the present invention.

References may be made to article entitled "Recovery of shikimic acid using temperature-swing complexation extraction and displacement back extraction" in Isolation & Purification, 1994, Vol. 2, pp. 75-82, wherein Miles et al. discloses a process for the removal of shikimic acid from aqueous solutions. The Miles et al. process is accomplished through solvent extraction using tridodecylamine dissolved in n-heptanol or n-butanol and back extraction to water using oleic acid to displace the shikimic acid from the organic phase. This reference focuses on developing a general method for recovering metabolic acids from fermentation broths. It fails, however, to disclose the use of acetic acid, which is added to a concentrated fermentation broth, to enhance the precipitation of shikimic acid from the broth.

An article from Synthesis of February, 1993 entitled: "The Biosynthesis and Synthesis of Shikimic Acid, Chorismic Acid and Related Compounds", pp. 179-193 by Campbell et al. teaches that compounds other than glyphosate may interfere, with the shikimic acid pathway. This article also provides a good description of the glucose derived shikimate pathway and the various arduous approaches to the chemical synthesis of shikimic acid. This article makes no suggestion regarding the isolation of highly pure PCCA from reaction mixtures through the use of concentrated acetic, lactic and/or propionic acids.

References may be made to Journal entitled: "Chemical Synthesis of Shikimic Acid and Its Analogues" in Tetrahedron Report Number 449, Vol. 54 (1998), pp. 4697-4753, wherein Jiang, et al. disclosed the complex and arduous task of the synthesis of shikimic acid and its analogues. Jiang, et al., like Campbell, et al, fails to disclose the present invention.

References may be made to U.S. Pat. No. 6,794,164, wherein Malmberg et al discloses a invention that has directed to the use of crystallization in acids, such as acetic, lactic and propionic acids, to obtain high purity polyhydroxylcyclic carboxylic acids (PCCA) from low purity aqueous solutions. The preferred PCCA is shikimic acid and the preferred crystallization acid is acetic acid. The method according to the invention is particularly applicable to the isolation of shikimic acid from a fermentation broth.

References may be made to patent application US20030138920, wherein Malmberg et al discloses an invention entitled Process for the isolation of polyhydroxy cyclic carboxylic acids. This invention is directed to the use of crystallization acids, such as acetic, lactic and propionic acids, to obtain high purity polyhydroxylcyclic carboxylic acids (PCCA) from low purity aqueous solutions. The preferred PCCA is shikimic acid and the preferred crystallization acid is acetic acid. The method according to the invention is particularly applicable to the isolation of shikimic acid from a fermentation broth.

In a report published in a web based encyclopaedia www.en.wikipedia.com, shikimic acid is extracted normally from chinese star anise with a yield of 3-7%. As found in the same report, another source of shikimic acid is seeds of sweetgum fruit found abundantly in North America, the yield of shikimic acid from this source are only 1.5%, Reference may also be made to the published report [Shende Jiang and Gurdial Singh, Chemical Synthesis of Shikimic Acid and Its Analogues, Tetrahedron report number 449, Tetrahedron 54 (1998) 4697-4753] wherein various methods of chemical synthesis of shikimic acid and its analogues are described. However, these methods are not suitable due to low yield and high cost of production.

In the pharmaceutical industry, shikimic acid from the Chinese star anise is used almost exclusively as a base material for production of Tami flu (oseltamivir). Tamiflu is the only drug available for the treatment of bird flu disease caused by avian influenza virus H5N1. Currently Tamiflu is produced starting from shikimic acid according to a technology Roche of Switzarland. Currently, due to recent outbreak of avian flu, tamiflu is required in 65 countries worldwide. Every year, it is estimated, required tamiflu will worth from Swiss franc 1.1 billion to 1.2 billion. (David Bradley, Star role for bacteria in controlling flu pandemic? Nature Reviews Drug Discovery, 2005, 4 (12), 945-946).

It is reported that triacyl shikimic acid derivatives can inhibit blood platelet assembling and Thrombosis by affecting the metabolism of Arachidonic acid (F. Huang; Q. Xiu; J. G Sun; H. Enrique; Anti-platelet and anti-thrombotic effects of triacetylshikimic acid in rats; Journal of cardiovascular pharmacology, 2002, vol. 39, No 2, pp. 262-270). According to a report in http://en.wikipedia.org/wiki/Shikimic_acid, in the pharmaceutical industry, shikimic acid from the Chinese star anise is used as a base material for production of Tamiflu (oseltamivir). Although shikimic acid is present in most autotrophic organisms, it is a biosynthetic intermediate and generally found in very low concentrations. The low isolation yield of shikimic acid from the Chinese star anise is responsible for the 2005 shortage of oseltamivir. Shikimic acid can also be extracted from the seeds of the sweetgum fruit (*Liquidambar styraciflua*), which is abundant in North America, in yields of around 1.5%, so just 4 kg of sweetgum seeds are enough for fourteen packages of Tamiflu. By comparison star anise has been reported to yield 3 to 7% shikimic acid. Recently biosynthetic pathways in *E. coli* have been enhanced to allow the organism to accumulate enough material to be used commercially (David Bradley, Star role for bacteria in controlling flu pandemic Nature Reviews Drug Discovery, 2005, 4 (12), 945-946).

According to a report published at the website www.livemint.com, China Government has currently imposed restriction on export of shikimic acid.

According to report the chemical composition of essential oils from several parts of a type of *Illicium griffithii* (short peduncle) harvested in Vietnam was investigated using GC, GC/MS and 13C-NMR spectroscopy. These oils contained mostly oxygenated phenylpropanoids, essentially safrole (51.6-65.3%) and 4-methoxysafrole (19.6%, root bark oil). Oils from aerial parts and bark of root oil differed significantly (Journal of Essential Oil Research: JEOR, January/February 2005 by Tam, Nguyen Thi, An, Ha Lai, Bighelli, Ange, Muselli, Alain, Casanova, Joseph).

Shikimic acid (3,4,5-trihydroxy-1-cyclohexene-1-carboxylic acid) has three (3) chiral centers, which make six (6) different optical isomers possible. A preferred product produced according to the present invention is the natural levorotatory L-shikimic acid of the structural formula 1.

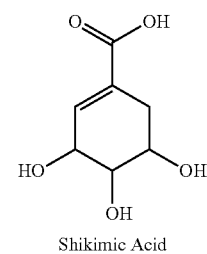

Shikimic Acid

Shikimic acid is an important new metabolic nutritional and starting material for antiviral, antibacterial and other therapeutic agents. While shikimic acid can be synthesized using various chemical routes, it is costly and presents difficulty in obtaining the proper stereoisomer. The compound can also be extracted from microorganism fermentation broth, but clean up and obtaining the high level of purity required is also problematic from this source. Present invention provides a method for the production of shikimic acid useful as raw material for the production of triacyl shikimic acid derivatives which can inhibit blood platelet assembling and Thrombosis by affecting the metabolism of Arachidonic acid. Present invention provides an alternative and commercially useful method than the hitherto known commercial methods of production of shikimic acid from the fruits of star anise (*Illicium verum*) and sweet gum (*Liquidambar styraciflua*) gives only 3-7% and 1.5% yield respectively. The process for obtaining shikimic acid from *Illicium griffithii* has been shown to be cost effective and practical. One aspect of the present invention provides an effective means to obtain high purity shikimic acid crystals from a crude aqueous alcoholic solution of shikimic acid. The process does not need the use of any acids, or elaborate temperature-swing complexation extractions and displacement back extractions.

OBJECTIVE OF THE INVENTION

The main objective of the present invention is to provide a method for the extraction of L-Shikimic acid from *Illicium griffithii* fruits with the yield of 12-18% w/w which obviates the drawbacks of the hitherto known prior art as detailed above.

Another object of the present invention is to provide a method for the extraction of shikimic acid useful for production of avian flu drug Tami flu (Oseltamivir).

Yet another object of the present invention is to provide a method for production of shikimic acid useful as raw material for the production of triacyl shikimic acid derivatives which inhibit blood platelet assembling and thrombosis by affecting the metabolism of arachidonic acid.

Yet another object of the method is to produce drug intermediate shikimic acid from the defatted fruits of *Illicium griffithii* and to remove semipolar compounds from the fruits *Illicium griffithii* before extracting shikimic acid

SUMMARY OF THE INVENTION

Accordingly, present invention provides a method for the extraction of high purity L-Shikimic acid from the fruits of *Illicium griffithii* and the said process comprising the steps of:
  i. powdering the fruits of *illicium griffithii* with a wind mill grinder;
  ii. extracting powdered fruit as obtained in step (i) with organic solvent with a soxhlet or soxhlet type apparatus to obtain defatted plant material;
  iii. extracting again defatted plant material as obtained in step (ii) with solvent to obtain defatted and solvent extracted plant material;
  iv. extracting defatted and solvent extracted plant material as obtained in step (iii) with polar solvent to obtain extract of solvent solvents;
  v. distillating solvent extract as obtained in step (iv) under reduced pressure in the range of 10 to 100 millibar and at temperature in the range of 30-100° C. to obtain crude shikimic acid;
  vi. dissolving crude shikimic acid as obtained in step (v) in alcohol;
  vii. heating and agitating the slurry as obtained in step (vi) at temperature in the range of 25° C. to the boiling point of the alcohol or to 90° C. for period in the range of 10-120 minutes;
  viii. cooling the solution as obtained in step (vii) at temperature in the range of 0 to −10° C. and maintaining for period in the range of 2 to 6 hours;
  ix. filtering the cooled solution as obtained in step (viii) followed by recrystallizing with aqueous methanol or ethanol to obtain pure crystalline shikimic acid. Optionally but not essentially, organic acid such as acetic acid can also be used for re-crystallization purpose to obtain pure crystalline shikimic acid.

In an embodiment of the present invention, organic solvent used for defatting fruits is hexane.

In another embodiment of the present invention, solvent used to remove semipolar compounds from fruits is selected from the group consisting of diethyl ether, chloroform, dichloromethane, ethylene dichloride or chlorinated hydrocarbon solvent more preferably chloroform.

In yet another embodiment of the present invention, polar solvent used is selected from the group consisting of methyl acetate, ethyl acetate, similar fatty acid ester(s), methanol, ethanol, propanol or combination thereof.

In yet another embodiment of the present invention, alcohol used is selected from the group consisting of methanol, ethanol, propanol, butanol or combination thereof.

In yet another embodiment of the present invention, yield of high purity L-shikimic acid is ranging between 12-18% w/w.

In yet another embodiment of the present invention, L-Shikimic acid is useful for production of avian flu drug Tami flu (Oseltamivir) and as starting materials for antibacterial, antifungal, herbicidal agents and as nutritional.

In yet another embodiment of the present invention, L-shikimic acid can also be isolated from dried powdered fruits of *Illicium griffithii* by defatting powdered fruits, extracting with methanol or ethanol or propanol, removal of the solvent from the extract solution and washing of the crude solid with chloroform followed by drying of crude solid shikimic acid under vacuum.

In yet another embodiment of the present invention, L-shikimic acid can also produced by extracting fruits of *Illicium griffithii* with supercritical carbon dioxide ($CO_2$) with any supercritical extractor, removal of the $CO_2$ from the extract, washing the solid extract with hexane or petroleum ether and then with chloroform to remove fatty and oily substances and then drying of solid shikimic acid under vacuum and recrystallized from aqueous methanol or ethanol to get pure shikimic acid. Optionally but not essentially, organic acid such as acetic acid can also be used for recrystallization purpose.

In yet another embodiment of the present invention, L-shikimic acid can also produced by extracting fruits of *Illicium griffithii* with boiling water, washing the water extract with hexane or petroleum ether and then with chloroform to remove fatty and oily substances and then removal of water by distillation under reduced pressure at 50-70° C. and recrystallization from methanolic water solution.

DETAILED DESCRIPTION OF THE INVENTION

A method for producing high purity crystals of Shikimic acid from the fruits of *Illicium griffithii* comprising (a) the fruits are powdered with a wind-mill (b) powdered fruits are then extracted with hexane with a soxhlet or soxhlet type apperatus. (c) the defatted plant material is then extracted with chloroform (d) the defatted and chloroform extracted plant material was thoroughly extracted with methyl acetate, ethyl acetate, or similar fatty acid ester(s) or low boiling alkanols like methanol, ethanol, propanol etc. (e) distillation of the ethyl acetate extract under reduced pressure in the range of 10 to 100 millibar at temperature in the range of 30 to 100° C. to get the crude shikimic acid. (f) The solid material containing mostly shikimic acid is then dissolved in methanol, ethanol, propanol, and the like (450 g crude shikimic acid per liter of alcohol). (g) Isolation of crystalline shikimic acid from the said concentrated solution.

Alternatively, fruits of *Illicium griffithii* can be extracted with boiling water and followed by removing fatty and oily substances by hexane or petroleum ether and chloroform and distillation of the extract at 50-70° C. to get pure shikimic acid.

Alternatively, fruits of *Illicium griffithii* can be extracted with supercritical carbon dioxide ($CO_2$) and followed by removing fatty and oily substances by hexane or petroleum ether and chloroform and drying of the extract under vacuum to get pure shikimic acid.

EXAMPLES

The following examples are given by way of illustration and therefore should not be construed to limit the scope of the present invention.

Example 1

54 g of dried fruits of *Illicium griffithii* were first ground into powder with a windmill grinder. The powdered fruits are then extracted with 150 ml of hexane with a soxhlet or soxhlet type apparatus. The defatted plant material is then extracted with 150 ml of chloroform. The defatted and chloroform extracted plant material was thoroughly extracted with 150 ml of methanol. Then the extracted methanol solution is distilled under reduced pressure at 20 millibar at below 50° C. (temperature was set at 50° C. and not allowed to rise above 50° C.) to get the crude shikimic acid. 20 ml of methanol was added to the solid material containing mostly shikimic acid and the mixture was refluxed for 30 minutes, cooled to 0° C. and maintained for 2 hours. The precipitated crystalline shikimic acid was then isolated by filtration. The yield obtained was 10 g (18.5% w/w, purity 99% by HPLC).

Example 2

500 g of dried fruits of *Illicium griffithii* were first ground into powder with a windmill grinder. The powdered fruits are then extracted with 2000 ml of hexane with a soxhlet or soxhlet type apparatus. The defatted plant material is then extracted with 2000 ml of chloroform. The defatted and chloroform extracted plant material was thoroughly extracted with 2000 ml of ethanol. Then the extracted ethanol solution was distilled under reduced pressure at 20 millibar at below 50° C. to get the crude shikimic acid. The solid material containing mostly shikimic acid is then dissolved in methanol, (105 g crude shikimic acid per 100 ml of alcohol). Concentrated solution of shikimic acid was cooled to 0° C. and maintained for 2 hours. Crystalline shikimic acid (88 g, 17.6%, purity 97% by HPLC) was then isolated by filtration.

Example 3

54 g of dried fruits of *Illicium griffithii* were first ground into powder with a windmill grinder. The powdered fruits are then extracted with 250 ml of hexane with a soxhlet or soxhlet type apparatus. The defatted plant material is then extracted with 250 ml of methanol. The methanol extract was then distilled under reduced pressure at 20 millibar at below 50° C. The solid obtained was then extracted with chloroform (10 ml of chloroform repeated 3 times). Chloroform washings were discarded. 20 ml of methanol was added to the solid material containing mostly shikimic acid and the mixture was refluxed for 30 minutes, cooled to 0° C. and maintained for 2 hours. Crystalline shikimic acid was then isolated by filtration and then dried under vacuum to get pure shikimic acid 9.5 g (17.6% w/w, purity 99% by HPLC).

Example 4

50 g of dried 5 year old fruits of *Illicium griffithii* were first ground into powder with a windmill grinder. The powdered fruits are then extracted with 200 ml of hexane with a soxhlet or soxhlet type apparatus. The defatted plant material is then extracted with 200 ml of methanol. The methanol extract was then distilled under reduced pressure at 20 millibar at below 50° C. (temperature was set at 50° C. and not allowed to rise above 50° C.). The solid obtained was then extracted with chloroform (10 ml×3, extracted three times with 10 ml of chloroform). Chloroform washings were discarded. 20 ml of methanol was added to the solid material containing mostly shikimic acid and the mixture was refluxed for 30 minutes, cooled to 0° C. and maintained for 2 hours. Crystalline shikimic acid was then isolated by filtration and then dried under vacuum to get pure shikimic acid 6.8 g (13.6% w/w, purity 99% by HPLC).

Example 5

50 g of dried fruits of *Illicium griffithii* were first ground into powder with a windmill grinder. The powdered fruits are then extracted with 200 ml of methanol with a soxhlet or soxhlet type apparatus. The methanol extract was then distilled under reduced pressure at 20 millibar at below 50° C. (temperature was set at 50° C. and not allowed to rise above 50° C.). The solids obtained were then extracted first with hexane (three times with 20 ml of hexane for each extraction) and then with chloroform (extracted three times with 10 ml of chloroform for each extraction). Hexane and Chloroform washings were discarded. 20 ml of methanol was added to the solid material containing mostly shikimic acid and the mixture was refluxed for 30 minutes, cooled to 0° C. and maintained for 2 hours. Crystalline shikimic acid was then isolated by filtration and then dried under vacuum to get pure shikimic acid 8.8 g (17.6% w/w, purity 99% by HPLC).

Example 6

50 g of dried fruits of *Illicium griffithii* were first ground into powder with a windmill grinder. The powdered fruits are then extracted with 200 ml of ethanol with a soxhlet or soxhlet type apparatus. The ethanol extract was then distilled under reduced pressure at 20 millibar at below 50° C. (temperature was set at 50° C. and not allowed to rise above 50° C.). The solids obtained were then extracted first with hexane (three times with 20 ml of hexane) and then with chloroform (extracted three times with 10 ml of chloroform for each extraction). Hexane and Chloroform washings were discarded. 20 ml of methanol was added to the solid material containing mostly shikimic acid and the mixture was refluxed for 30 minutes, cooled to 0° C. and maintained for 2 hours. Crystalline shikimic acid was then isolated by filtration and then dried under vacuum to get pure shikimic acid 8 g (16% w/w, purity 99% by HPLC).

Example 7

50 g of dried fruits of *Illicium griffithii* were first ground into powder with a windmill grinder. The powdered fruits are then extracted with 200 ml of propanol with a soxhlet or soxhlet type apparatus. The propanol extract was then distilled under reduced pressure at 20 millibar at below 50° C. (temperature was set at 50° C. and not allowed to rise above 50° C.). The solids obtained were then extracted first with hexane (three times with 20 ml of hexane) and then with chloroform (extracted three times with 10 ml of chloroform for each extraction). Hexane and Chloroform washings were discarded. 20 ml of methanol was added to the solid material containing mostly shikimic acid and the mixture was refluxed for 30 minutes, cooled to 0° C. and maintained for 2 hours.

Crystalline shikimic acid was then isolated by filtration and then dried under vacuum to get pure shikimic acid 8 g (16% w/w, purity 97% by HPLC).

Example 8

50 g of dried fruits of *Illicium griffithii* were first ground into powder with a windmill grinder. The powdered fruits are then extracted with 200 ml of water with a soxhlet or soxhlet type apparatus. The aqueous solution obtained was allowed to cool to room temperature and then extracted first with hexane (three times with 20 ml of hexane for each extraction) and then with chloroform (extracted three times with 10 ml of chloroform for each extraction). Hexane and Chloroform washings were discarded. The water extract was then distilled under reduced pressure at 20 millibar at 50° C. to 70° C. and not allowed to rise above 70° C. 20 ml of methanol was added to the solid obtained containing mostly shikimic acid and the mixture was refluxed for 30 minutes, cooled to 0° C. and maintained for 2 hours. Crystalline shikimic acid was then isolated by filtration and then dried under vacuum to get pure shikimic acid 7.8 g (15.6% w/w, purity 95% by HPLC).

Example 9

50 g of dried fruits of *Illicium griffithii* were first ground into powder with a windmill grinder. The powdered fruits are then extracted with 200 ml of supercritical $CO_2$ with a supercritical extractor. The $CO_2$ was then allowed to evaporate from the extract to give a solid, which is usually in powdered form. The solids obtained were then extracted first with hexane (three times with 20 ml of hexane) and then with chloroform (extracted three times with 10 ml of chloroform for each extraction). Hexane and Chloroform washings were discarded. 20 ml of methanol was added to the solid material containing mostly shikimic acid and the mixture was refluxed for 30 minutes, cooled to 0° C. and maintained for 2 hours. Crystalline shikimic acid was then isolated by filtration and then dried under vacuum to get pure shikimic acid 8.7 g (17.4% w/w, purity 97% by HPLC).

Example 10

54 g of dried fruits of *Illicium griffithii* were first ground into powder with a windmill grinder. The powdered fruits are then extracted with 150 ml of hexane with a soxhlet or soxhlet type apparatus. The defatted plant material is then extracted with 150 ml of chloroform. The defatted and chloroform extracted plant material was thoroughly extracted with 150 ml of methanol. Then the extracted methanol solution is distilled under reduced pressure at 100 millibar using water-bath at bath temperature of 100° C. to get the crude shikimic acid. 20 ml of aqueous methanol (1:1) was added to the solid material containing mostly shikimic acid and the mixture was refluxed for 30 minutes, cooled to −10° C. and maintained for 6 hours. The precipitated crystalline shikimic acid was then isolated by filtration. The yield obtained was 9 g (16.6% w/w, purity 95% by HPLC).

Example 11

50 g of dried fruits of *Illicium griffithii* were first ground into powder with a windmill grinder. The powdered fruits are then extracted with 150 ml of hexane with a soxhlet or soxhlet type apparatus. The defatted plant material is then extracted with 150 ml of chloroform. The defatted and chloroform extracted plant material was thoroughly extracted with 150 ml of methanol. Then the extracted methanol solution is distilled under reduced pressure at 10 millibar using water-bath at bath temperature of 30° C. to get the crude shikimic acid. 20 ml of aqueous ethanol (1:1) was added to the solid material containing mostly shikimic acid and the mixture was refluxed for 120 minutes, cooled to −10° C. and maintained for 6 hours. The precipitated crystalline shikimic acid was then isolated by filtration. The yield obtained was 9 g (18% w/w, purity 99% by HPLC).

ADVANTAGES OF THE INVENTION

In the pharmaceutical industry, shikimic acid from the Chinese star anise is used as a base material for the production of Tamiflu (oseltamivir). Although shikimic acid is present in most autotrophic organisms, it is a biosynthetic intermediate and generally found in very low concentrations. The low isolation yield of shikimic acid from the Chinese star anise is responsible for the 2005 shortage of oseltamivir. Further, as per report published at the website www.livemint.com, China Government has imposed restriction on export of shikimic acid. Shikimic acid can also be extracted from the seeds of the sweet gum fruit, which is abundant in North America, in yields of around 1.5%. By comparison star anise has been reported to yield 3 to 7% shikimic acid. Recently biosynthetic pathways in *E. coli* have been enhanced to allow the organism to accumulate enough material to be used commercially.

Process gives a commercially highly viable method for the production of shikimic acid which can be used as base material for the production of avian flu drug Tami flu.

We claim:

1. A method for the extraction of high purity L-Shikimic acid from the fruits of *Illicium griffithii* and the said process comprising the steps of:
   i. powdering the fruits of *illicium griffithii* with a wind mill grinder;
   ii. extracting powdered fruit as obtained in step (i) with organic solvent with a soxhlet or soxhlet type apparatus to obtain defatted plant material;
   iii. extracting again defatted plant material as obtained in step (ii) with solvent to obtain defatted and solvent extracted plant material;
   iv. extracting defatted and solvent extracted plant material as obtained in step (iii) with polar solvent to obtain solvent extract;
   v. distilling solvent extract as obtained in step (iv) under pressure in the range of 10 to 100 millibar and at temperature in the range of 30-100° C. to obtain crude shikimic acid;
   vi. dissolving crude shikimic acid as obtained in step (v) in alcohol;
   vii. heating and agitating the slurry as obtained in step (vi) at temperature in the range of 25° C. to the boiling point of the alcohol or to 90° C. for period in the range of 10-120 minutes;
   viii. cooling the solution as obtained in step (vii) at temperature in the range of 0 to −10° C. and maintaining for period in the range of 2 to 6 hours;
   ix. filtering the cooled solution as obtained in step (viii) followed by recrystallizing with aqueous methanol or aqueous acetic acid to obtain pure crystalline shikimic acid.

2. A method as claimed in claim 1, wherein the organic solvent used in step (ii) for defatting fruits is hexane, petroleum ether, or a hydrocarbon solvent.

3. A method as claimed in claim 1, wherein the solvent used in step (iii) for removal of semipolar compounds from fruits is selected from the group consisting of diethyl ether, chloroform, dichloromethane, ethylene dichloride or chlorinated hydrocarbon solvent, more preferably chloroform.

4. A method as claimed in step (iv) of claim 1, wherein the polar solvent used is selected from the group consisting of methyl acetate, ethyl acetate, similar fatty acid ester(s), methanol, ethanol, propanol or combination thereof.

5. A method as claimed in step (vi) of claim 1, wherein alcohol used is selected from the group consisting of methanol, ethanol, propanol, butanol or combination thereof.

6. A method as claimed in claim 1, wherein yield of high purity L-shikimic acid is ranging between 12-18% w/w.

7. A method as claimed in claim 1, wherein the L-Shikimic acid is further used in production of avian flu drug Tami flu (Oseltamivir) and as starting materials for antibacterial, antifungal, herbicidal agents and as nutritional.

\* \* \* \* \*